United States Patent
Hecht (10) Patent No.: US 8,061,037 B2
(45) Date of Patent: Nov. 22, 2011

(54) METHOD FOR FORMING MONITORED CONCRETE PILINGS USING A POUR DIVERTER

(75) Inventor: Kurt Hecht, New Hope, PA (US)

(73) Assignee: Smart Structures, Inc., Southampton, PA (US)

( * ) Notice: Subject to any disclaimer, the term of this patent is extended or adjusted under 35 U.S.C. 154(b) by 1217 days.

(21) Appl. No.: 11/611,445

(22) Filed: Dec. 15, 2006

(65) Prior Publication Data

US 2007/0151103 A1 Jul. 5, 2007

Related U.S. Application Data

(60) Provisional application No. 60/750,510, filed on Dec. 15, 2005.

(51) Int. Cl.
*B21D 49/00* (2006.01)

(52) U.S. Cl. ........ 29/897.34; 29/458; 29/460; 29/527.1; 29/527.2; 29/897; 29/897.33; 52/742.1; 52/742.14; 52/742.13; 73/803; 264/31

(58) Field of Classification Search ............. 29/897, 29/460, 527.1, 897.33, 897.34, 458, 527.2; 52/745.13, 259, 741.1; 73/803, 11.03; 264/27, 264/31; 405/232, 229; 340/853.8
See application file for complete search history.

(56) References Cited

U.S. PATENT DOCUMENTS

| | | | |
|---|---|---|---|
| 2,267,024 A | 12/1941 | Goodwin | |
| 3,922,124 A | 11/1975 | Bjorhaag | |
| 4,052,884 A | 10/1977 | Milberger et al. | |
| 4,171,563 A | 10/1979 | Withoos | |
| 4,588,082 A | 5/1986 | Ridings | |
| 4,943,930 A | 7/1990 | Radjy | |
| 5,126,751 A | 6/1992 | Wada et al. | |
| 5,367,854 A * | 11/1994 | Kim | 52/745.13 |
| 5,581,013 A | 12/1996 | Frederick | |
| 5,978,749 A | 11/1999 | Likins, Jr. et al. | |
| 6,127,937 A | 10/2000 | Carlini, Jr. | |
| 6,301,551 B1 | 10/2001 | Piscalko et al. | |
| 6,533,502 B2 * | 3/2003 | McVay et al. | 405/232 |
| 6,772,091 B1 | 8/2004 | Roberts | |
| 6,796,187 B2 | 9/2004 | Srinivasan et al. | |
| 2006/0021447 A1 | 2/2006 | Hecht et al. | |

FOREIGN PATENT DOCUMENTS

AT 397630 5/1994

* cited by examiner

*Primary Examiner* — Richard Chang
(74) *Attorney, Agent, or Firm* — Volpe and Koenig, P.C.

(57) ABSTRACT

A method for casting monitored pilings and a pour diverter used in connection with the method is provided. The method includes positioning a plurality of pile strands in a form, and then connecting a suspension assembly having at least one sensor to at least one of the pile strands so that the at least one sensor is located in a piling core area. A pour diverter, having a generally V-shaped configuration, is positioned over the suspension assembly. Concrete is poured into the form over the pour diverter so that a flow of the concrete into the form is split and flows down on either side of the suspension assembly until the at least one sensor is covered. The pour diverter is then removed to finish the casting. Preferably, provisions are provided on the pour diverter for holding or covering an antenna assembly during the pour, prior to it being placed into the concrete forming the piling.

11 Claims, 15 Drawing Sheets

METHOD FOR FORMING MONITORED CONCRETE PILINGS USING A POUR DIVERTER

CROSS-REFERENCE TO RELATED APPLICATIONS

This application claims the benefit of U.S. Provisional Application No. 60/750,510, filed Dec. 15, 2005.

BACKGROUND

The invention relates to a pour diverter and method for forming concrete pilings and structures having gauges and sensors pre-cast therein. Pilings of this type are described in the inventors' prior co-pending U.S. Patent Application, published as US2006/0021447.

It would be desirable to provide a more efficient and cost effective method for casting and manufacturing such concrete structures. It would be desirable to protect an embedded monitoring system from damage during the casting and manufacturing process, while still allowing for fast and efficient construction.

SUMMARY

In accordance with the invention, these objectives are met through the use of a pour diverter in connection with the casting of the monitored pilings. The method according to the invention includes positioning and preferably tensioning a plurality of pile strands in a form, and then connecting a suspension assembly having at least one sensor to at least one of the pile strands so that the at least one sensor is located in a piling core area. A pour diverter, preferably having a generally V-shaped configuration, is positioned over the suspension assembly. Concrete is poured into the form over the pour diverter so that a flow of the concrete into the form is split and flows down on either side of the suspension assembly until the at least one sensor is covered. The pour diverter is then removed to finish the casting.

Preferably, provisions are provided on the pour diverter for holding or protecting an antenna assembly during the pour, prior to it being placed in the concrete once the form is filled.

The method and pour diverter according to the invention thus provides an economical manner to protect the sensors, suspension assembly and associated wiring from damage which can be caused by a direct flow of concrete during casting that cannot be corrected after the concrete has been poured, and generally remains unknown until the monitored piling is tested. This reduces defects and does not negatively affect productivity or through-put in casting the pilings. The diverter also provides a means to get concrete in and around the sensors rapidly, in a void-free manner and consistently without subjecting the sensors to flow related stresses.

DETAILED DESCRIPTION OF THE PREFERRED EMBODIMENT(S)

Certain terminology is used in the following description for convenience only and is not limiting. The words "right," "left," "top," and "bottom" designate directions in the drawings to which reference is made. The words "a" and "one" are defined as including one or more of the referenced item unless specifically stated otherwise. This terminology includes the words above specifically mentioned, derivatives thereof, and words of similar import. The phrase "at least one" followed by a list of two or more items, such as A, B, or C, means any individual one of A, B or C as well as any combination thereof. U.S. patent application Ser. No. 11/188,492, published as US2006/0021447 which is subject to assignment to the same assignee as the present application, provides disclosure relevant to the description below and is incorporated by reference as if set forth fully herein.

Figure 1:
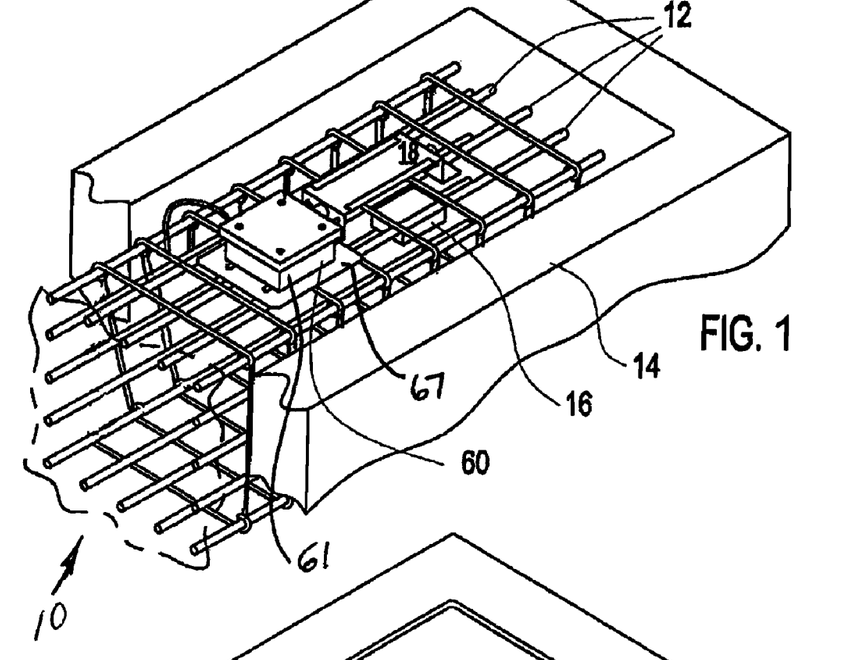
FIG. 1 is a perspective view showing strands in a piling form prior to casting concrete into the form in order to form the piling.

Referring to FIG. 1, strands 12 for a piling 10 are shown positioned in a piling form 14 prior to casting concrete in the form 14 in order to form the piling. Sensors 16 and an antenna assembly 18 for transmitting data from the piling during or after installation are shown connected to or suspended from or above the strands 12, preferably using cable ties or similar holding devices. Sensors and antennas are preferably used for monitoring of the pilings using a direct wireless data transfer of data being gathered by the sensors embedded in the pilings as described in detail below, for installation and/or lifetime monitoring of the piling as well as also possibly for storing piling data.

FIG. 1 shows a first embodiment of an antenna assembly 60 which also includes a radio temporarily located lying on top of the pile strands 12, which will float in the concrete that is cast in the form so that a top surface of the antenna/radio assembly 60 is located on a surface of the piling. Additionally, the sensors 16 are attached to a preferred suspension assembly as explained in further detail below in order to position the sensors 16 between the pile strands 12.

Figure 2:
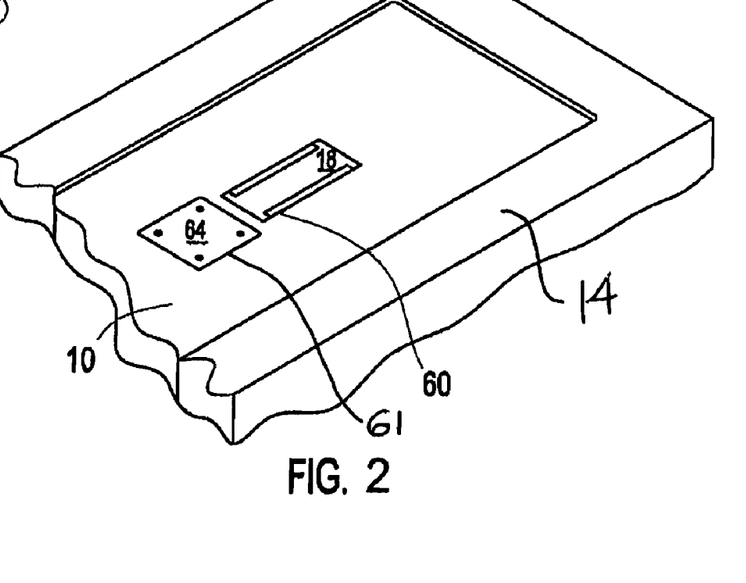
FIG. 2 is a perspective view showing the piling form after the concrete has been cast into the form.

FIG. 2 shows the piling 10 cast in the form 14 after the concrete has been poured. The surface of the antenna 18 remains generally flush and exposed for signal transmission before, during and/or after the pile drive. Also, the cover 64 of the antenna/radio assembly 60 remains exposed. It is also possible to remove the antenna 18 and incorporate the antenna into the cover 64 of the electronics module housing 61.

Figure 3:
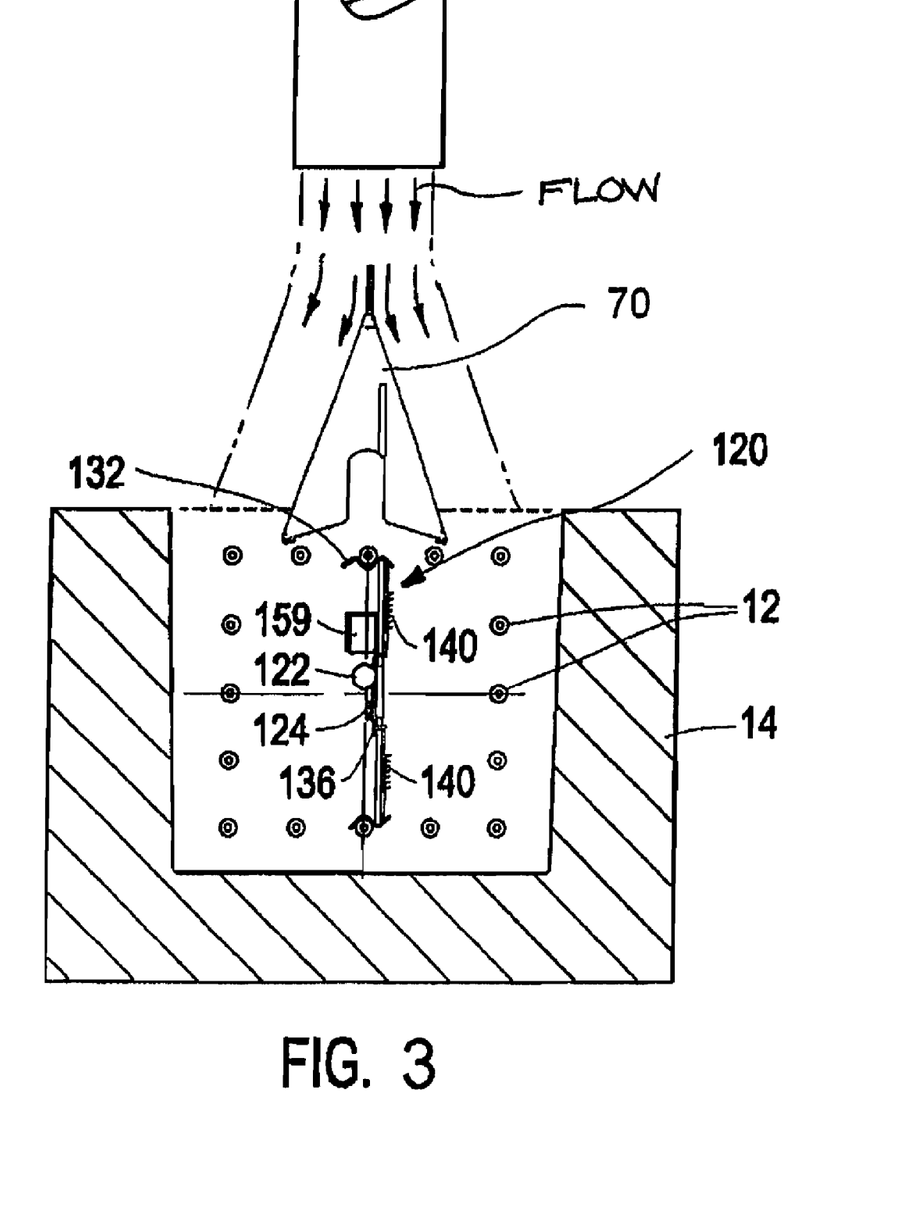
FIG. 3 is a cross-sectional view through the piling form of FIG. 1 showing the strands and a pour diverter, according to a preferred embodiment of the invention, positioned over a U-Bar suspension assembly for mounting of sensors in the piling.
Figures 4, 5, 6, 7, 8:
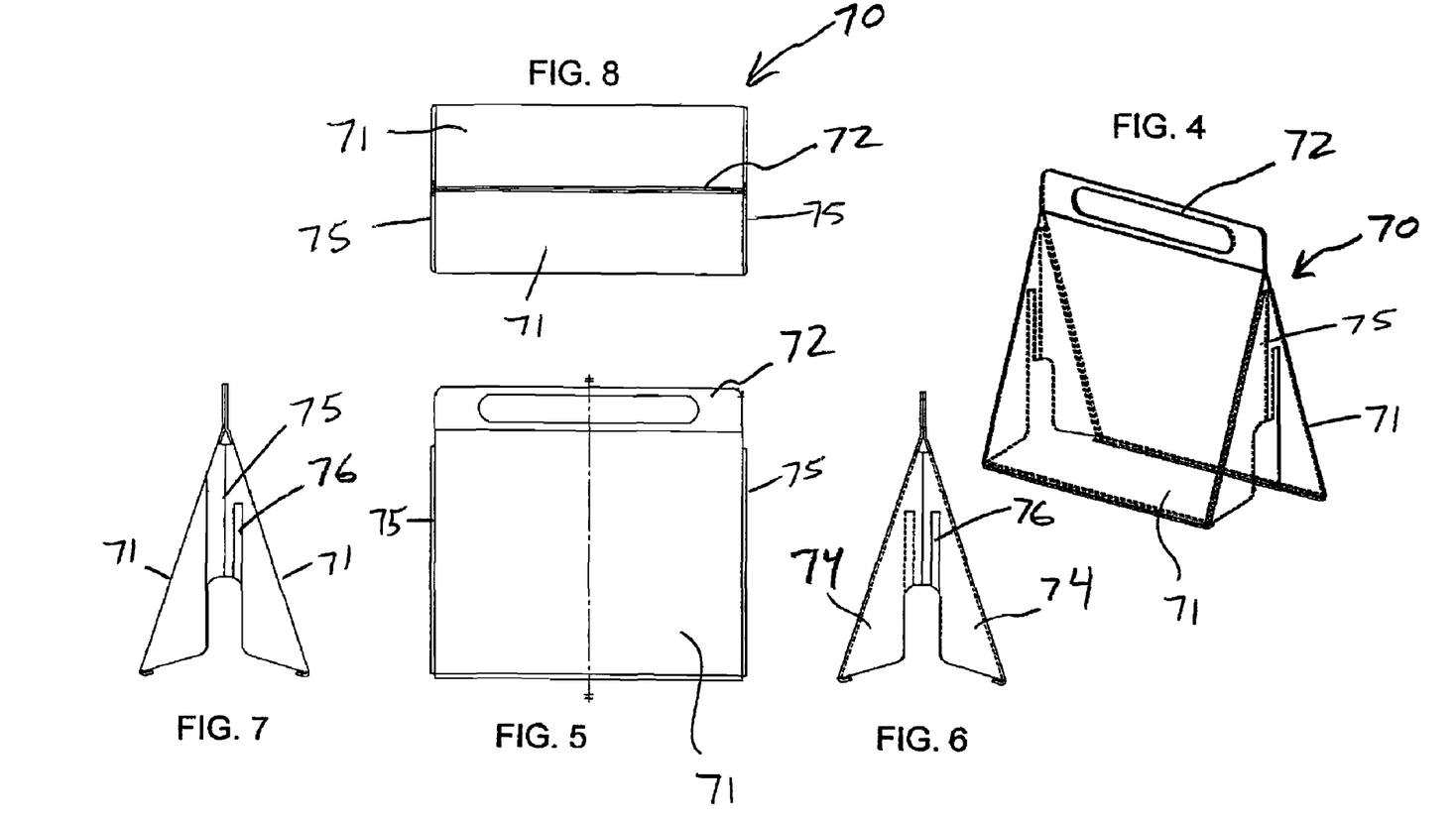
FIG. 4 is a perspective view of the pour diverter shown in FIG. 3.
FIG. 5 is a side elevational view of the pour diverter of FIG. 4.
FIG. 6 is a front elevational view of the pour diverter of FIG. 4.
FIG. 7 is a rear elevational view of the pour diverter of FIG. 4.
FIG. 8 is a top plan view of the pour diverter of FIG. 4.

As shown in FIG. 3, in accordance with the present invention a U-Bar suspension assembly 120 is preferably installed generally vertically in the piling form 14 in order to facilitate fast, accurate and repeatable positioning of the sensors located thereon. Preferably, this includes an accelerometer 122 and a strain gauge 124, which must be positioned cross-sectionally within the piling core. The U-Bar suspension assembly 120 is preferably spring loaded and provides for repeatable positioning of the sensors within a center of the core area of the piling form 14 while minimizing the need for hand measurements and maintaining the accelerometer in a position orthogonal to the piling length in order to allow accurate acceleration measurements during subsequent driving of the piling, and also maintaining the strain gauge in a position parallel to a longitudinal axis of the piling to ensure accurate strain measurements. The preferred embodiments of the U-Bar suspension assembly and its preferred installation are described in detail in the incorporated U.S. patent application Ser. No. 11/188,492.

One problem encountered with the installation of the sensors shown in FIGS. 1-3 is that during pouring of the concrete, there is a potential for damage and movement of the sensors 122, 124 and wiring due to the stress and forces caused by a direct flow of fluid concrete passing over the sensors 122, 124. The suspension assembly 120 is also at risk of being dislocated from its measured position between the strands 12. Positioning of the sensors 122, 124 is critical to the integrity of the data, and therefore cannot be lost. Further, the antenna assembly 18, which in its horizontal mounting position presents a large profile around which concrete must be poured, is at significant risk of damage during the pouring process. Typically, during casting of pilings, concrete is poured in a linear fashion down the center of the form, starting at one end and running to the other end. The forms typically are hundreds of feet long, and include multiple pilings that are formed end to end. As shown in FIG. 3, a pour diverter 70 is positioned on the strands 12 of the piling 10 prior to casting concrete in the form 14 in order to divert liquid concrete away, in a side-to-side manner, from the suspension assembly during pouring. This means the concrete is still delivered in a linear fashion to the form, with the pour progressing down the form, but at the diverter location, the concrete pour is divided into two side-to-side flows by the diverter 70 until the concrete reaches a sufficient level to cover the sensors 122, 124 on the suspension assembly 120.

Referring to FIGS. 4-8, the pour diverter 70 is preferably V-shaped with two diverter sides 71 to promote generally unobstructed flow thereover. Alternatively the diverter 70 can be formed in any other suitable shape. A handle portion 72 is preferably provided to facilitate carrying and positioning of the diverter 70. Slots 76 are preferably provided on each of the two ends 75 of the diverter 70 to allow the diverter 70 to receive a cooperating portion of the antenna/radio assembly 60, as discussed below. Those skilled in the art will recognize that other antenna holding features can be provided, such as clamps, clips or hangers. The diverter 70 is preferably constructed of two identical formed metal parts 74 welded together. Alternatively, the diverter 70 can be fabricated from wood, plastic, composite or any suitable material using any suitable construction method.

Figure 9:
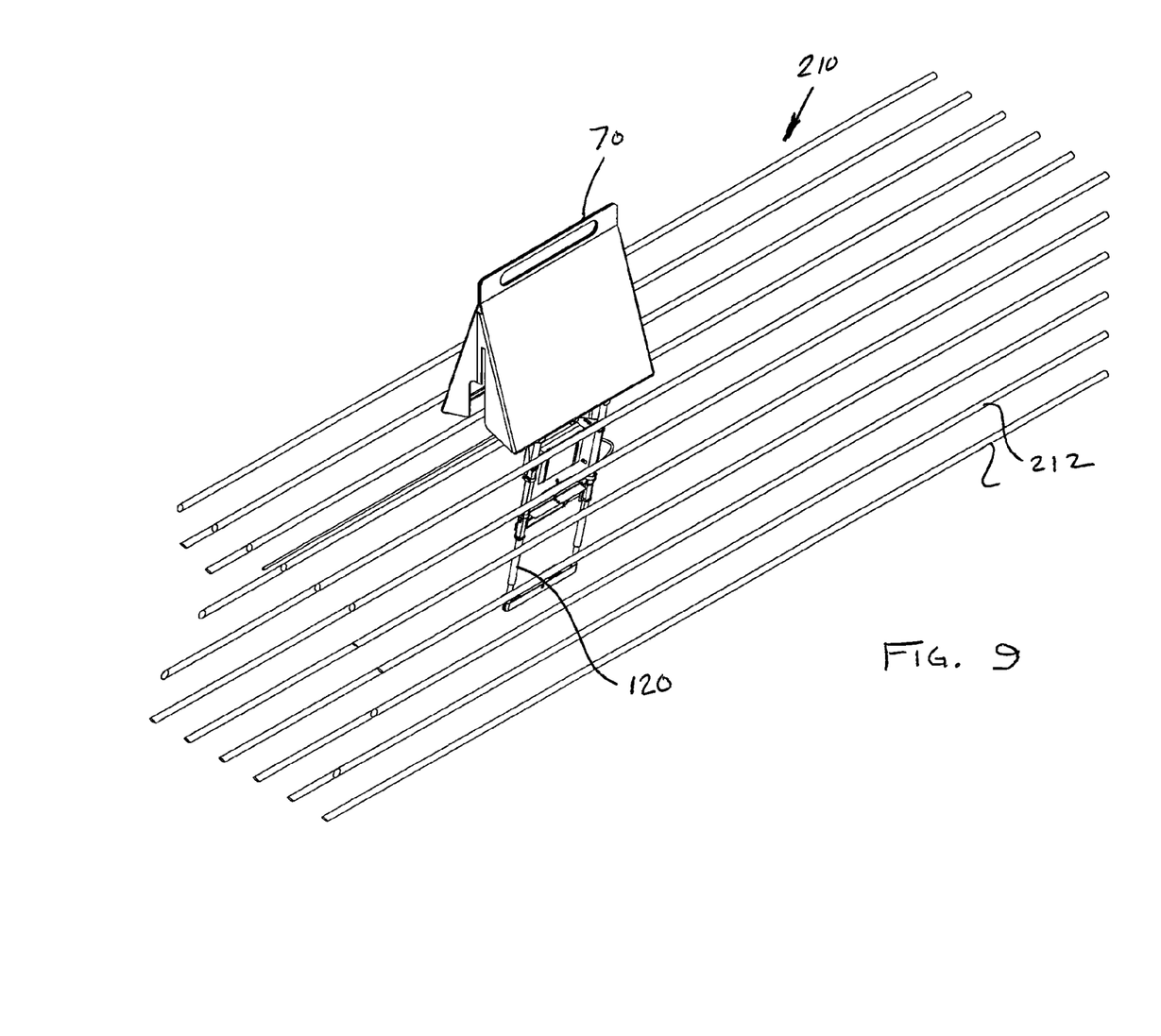
FIG. 9 is a perspective view of a portion of a piling prior to concrete casting including a U-bar suspension assembly and a pour diverter according to the preferred embodiment of the invention.
Figure 10:
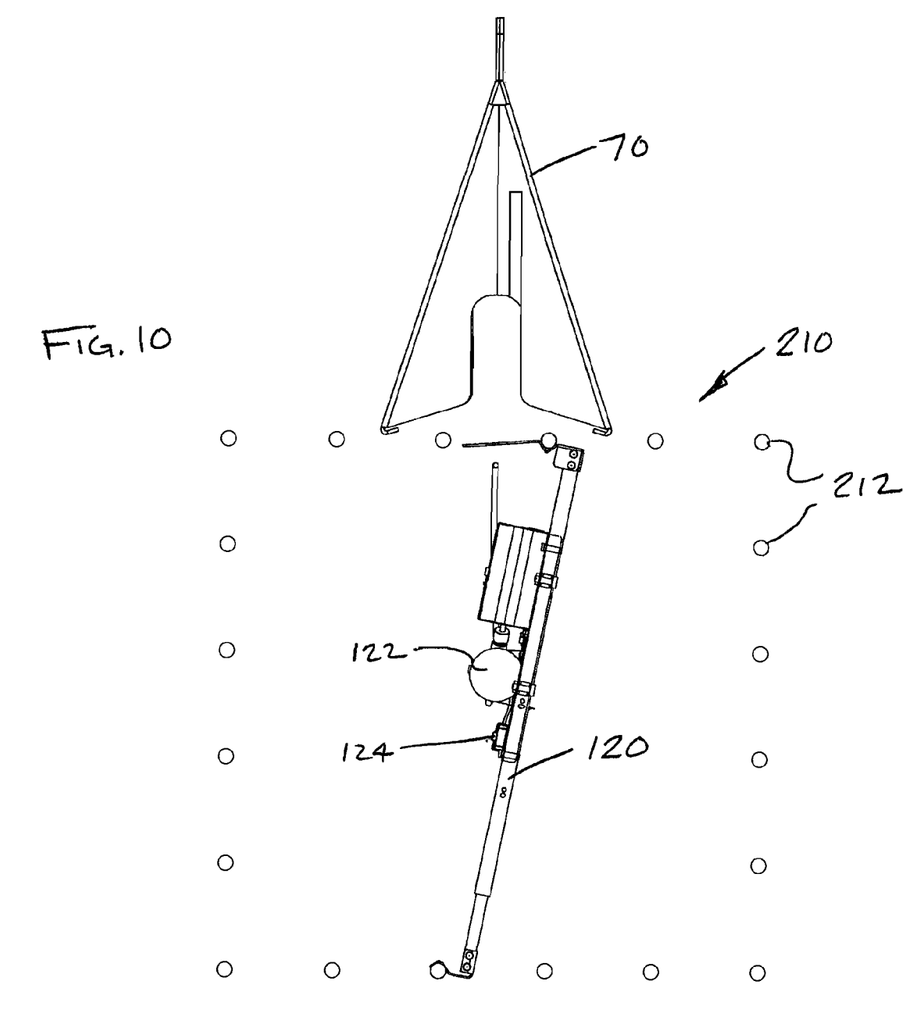
FIG. 10 is a front elevational view of the piling portion of FIG. 9.
Figure 11:
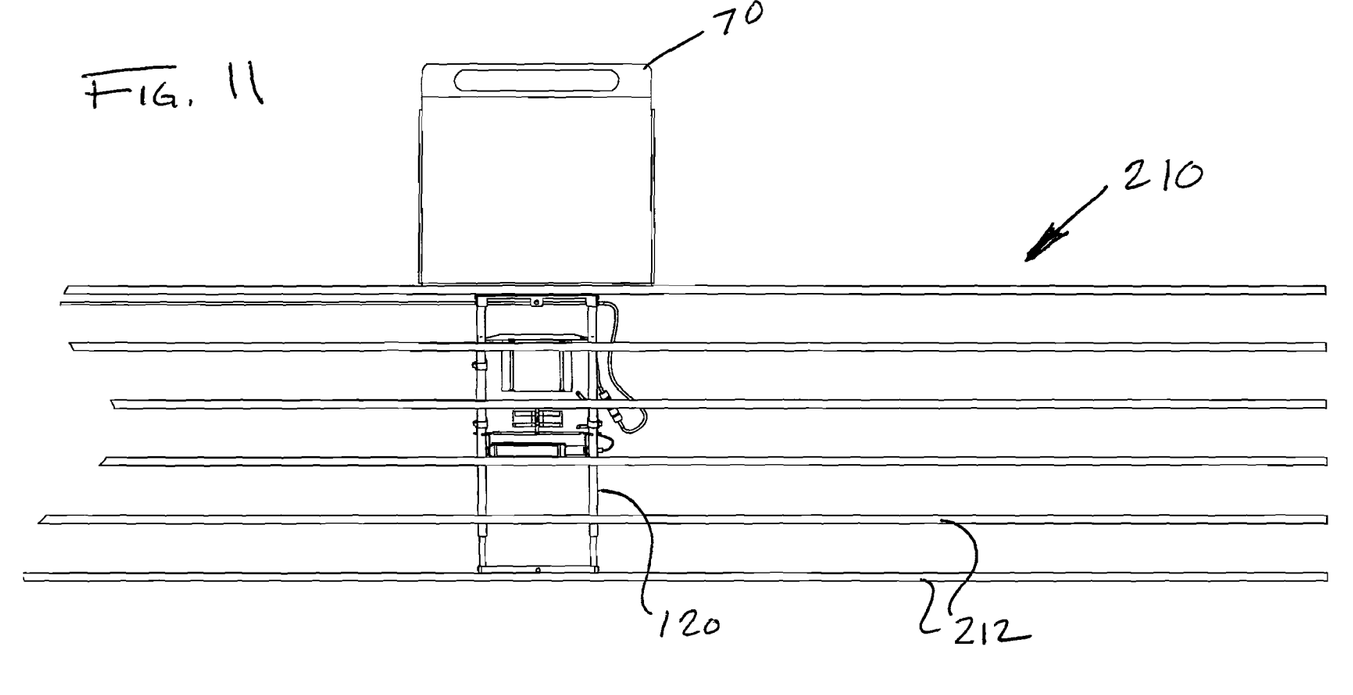
FIG. 11 is a side elevational view of the piling portion of FIG. 9.

Referring to FIGS. 9-11, a portion of a piling 210 shown prior to concrete casting includes the U-bar suspension assembly 120 and the pour diverter 70 according to the preferred embodiment of the present invention. In the piling portion 210, the U-bar suspension assembly 120 is positioned slightly angled from vertical due to the positions of the strands 212.

Figure 24:
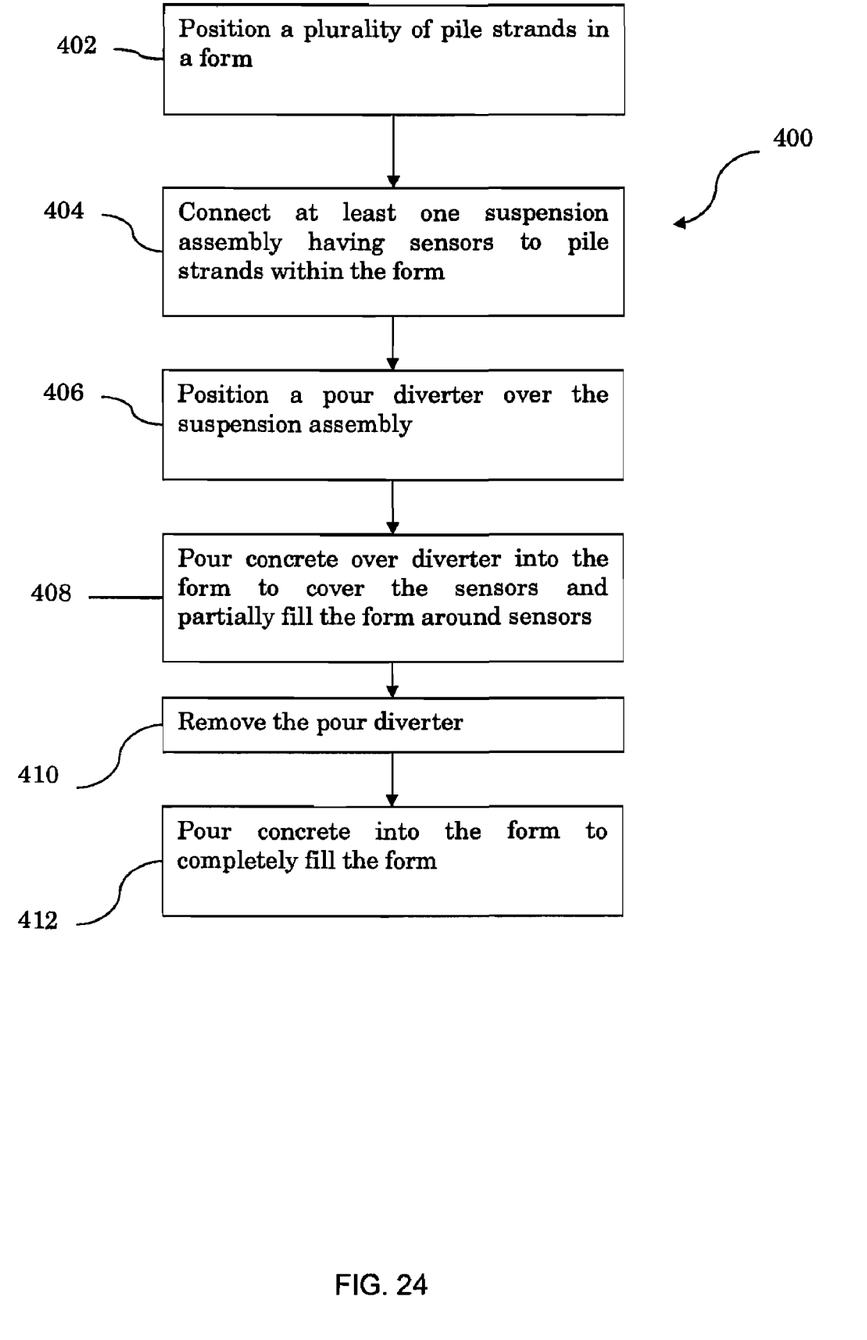
FIG. 24 is a flowchart showing a method for casting a piling according to a preferred embodiment of the present invention.

Referring to FIG. 24, a flow chart describing a method 400 for casting a piling 210 or section thereof according to a preferred embodiment of the present invention is shown. The method includes positioning and tensioning a plurality of pile strands in a form (step 402) and connecting a suspension assembly 120 including one or more sensors to the strands (step 404). A pour diverter 70 is centrally positioned over the suspension assembly 120, preferably in contact with one or more of the strands 212 or the internal steel structure of the pile 210, to protect the sensors during the pour process (step 406). Concrete is poured into the form (step 408) to at least partially fill the form. Preferably, the form is filled to a level just below the diverter 70, or at least covering the sensor/gauges on the suspension assembly 120. During the pouring process, concrete can be poured directly over the diverter 70 to split the material flow from side-to-side to more thoroughly fill areas of the form in proximity to the suspension assembly 120. After partially filling the form, the pour diverter 70 is removed (step 410), and the form is completely filled to a desired level with concrete (step 412).

Figure 12:
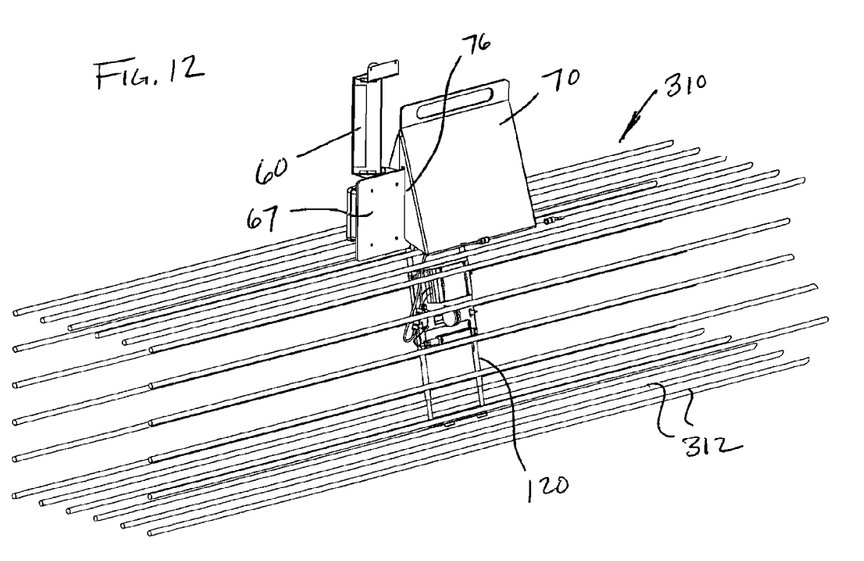
FIG. 12 is a perspective view of a portion of a piling prior to concrete casting including a U-bar suspension assembly, an antenna/radio assembly and a pour diverter according to the preferred embodiment of the invention.
Figure 13:
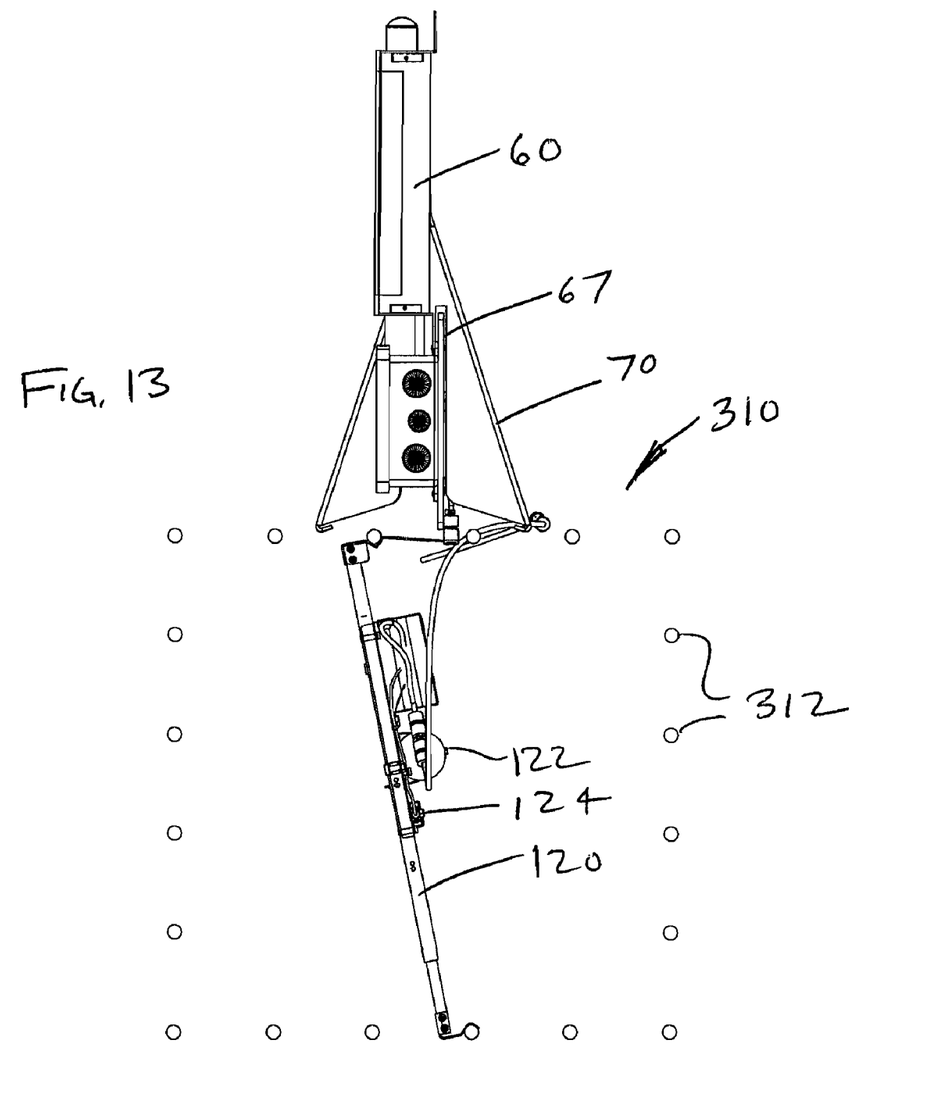
FIG. 13 is a front elevational view of the piling portion of FIG. 12.
Figure 14:
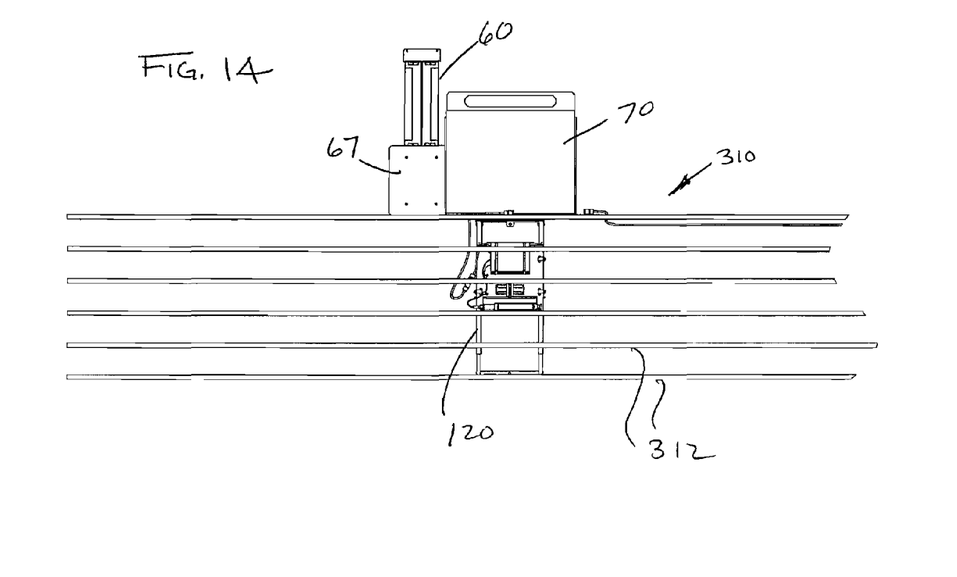
FIG. 14 is a side elevational view of the piling portion of FIG. 12.

Referring to FIGS. 12-14, a portion of a piling 310 shown prior to concrete casting includes the U-bar suspension assembly 120 and the pour diverter 70 according to the preferred embodiment of the present invention. In the piling portion 310, the U-bar suspension assembly 120 is positioned slightly angled from vertical due to the position of the strands 312. An antenna assembly 60 with a radio, as shown in FIGS. 1 and 2, is positioned in proximity to the U-bar suspension assembly 120. A buoyancy compensation plate 67 of the antenna/radio assembly 60 is aligned in one of the slots 76 of the pour diverter 70 to position the antenna/radio assembly 60 in a vertical, outwardly extending position. This position reduces an exposed horizontal area of the antenna/radio assembly 60, such that during the pouring process, the antenna/radio assembly 60 is potentially less exposed to poured concrete. It also protects the wires and connectors from damage by positioning them under the hollow cover formed by the underside of the diverter 70.

Figure 15:
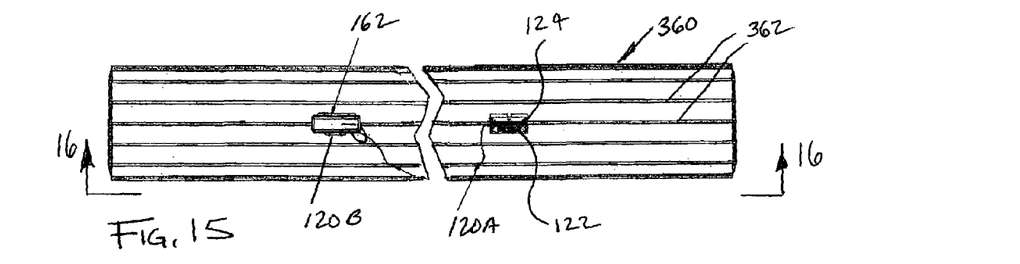
FIG. 15 is a side view of a piling showing a tip sensor package and a top sensor package with radio and a surface mount antenna positioned in a piling.
Figure 16:
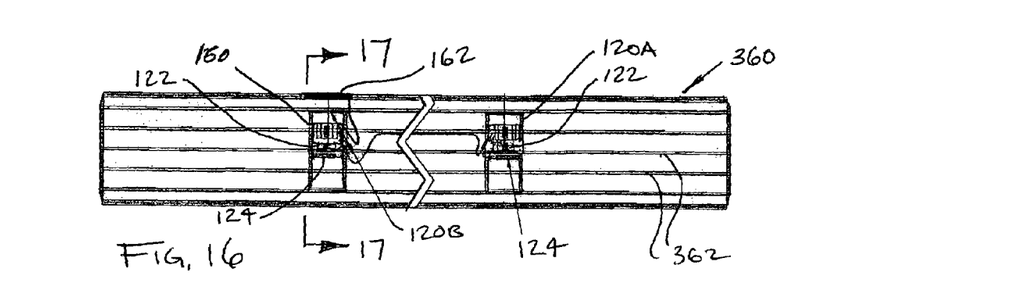
FIG. 16 is a view of the piling taken along line 16-16 in FIG. 15.
Figure 17:
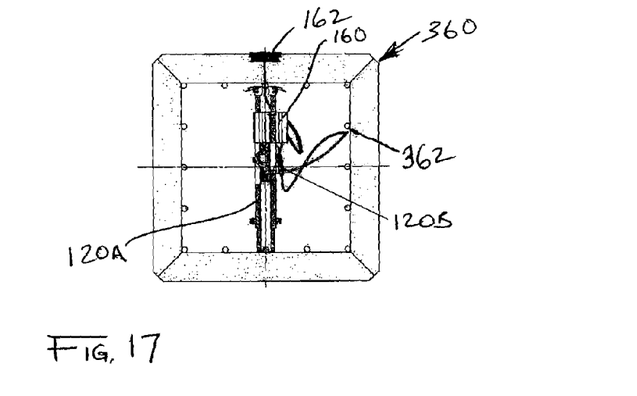
FIG. 17 is a cross-sectional view through the piling of FIG. 16 taken along line 17-17.
Figure 18:
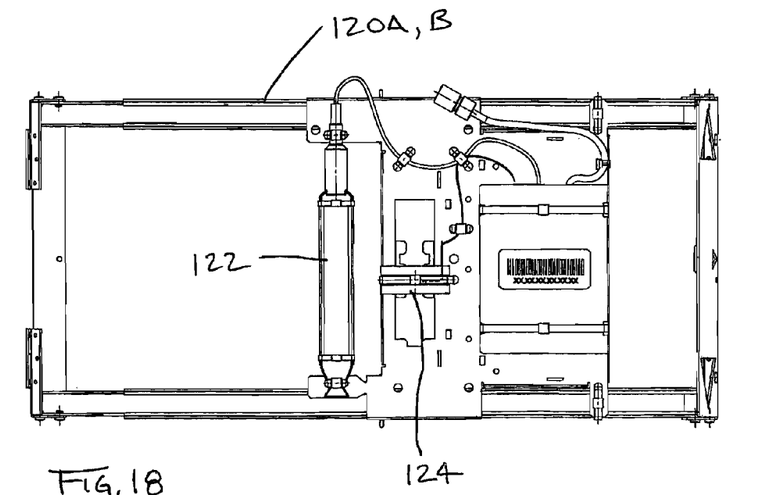
FIG. 18 is a plan view of a suspension assembly for the sensors
Figure 19:
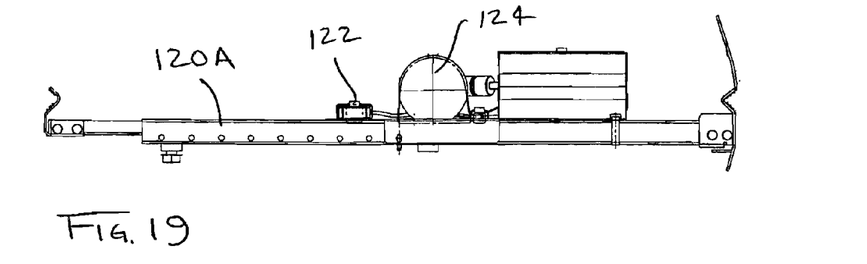
FIG. 19 is a side view of the suspension assembly of FIG. 18 without a radio, preferably for use at a piling tip.
Figure 20:
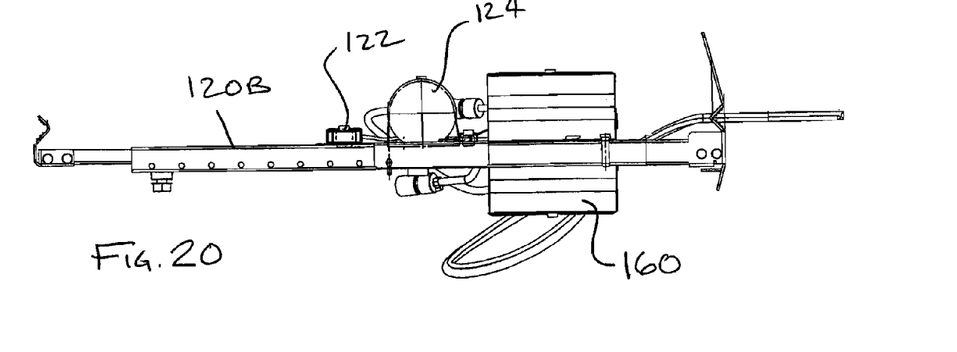
FIG. 20 is a side view of the suspension assembly of FIG. 18 with a radio for use in connection with an antenna to transmit piling data from the sensors.
Figure 21:
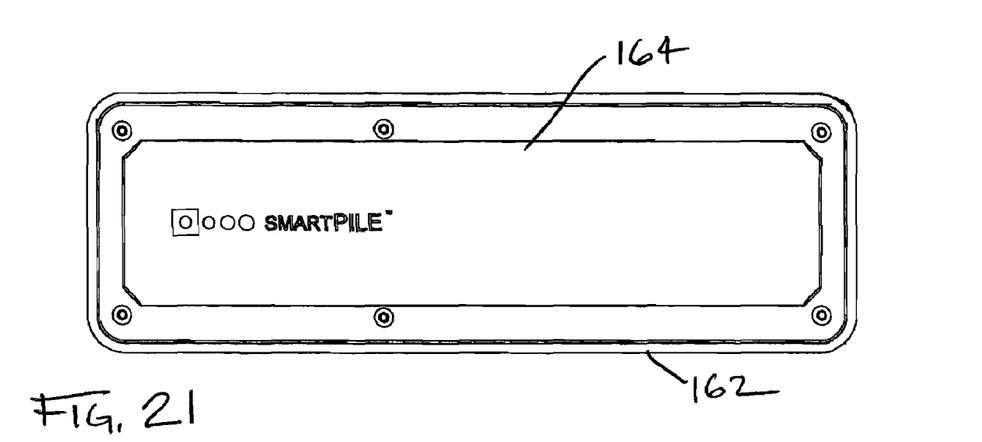
FIG. 21 is a top view of an alternate embodiment of an antenna for use in the piling of FIGS. 15-17.
Figure 22:
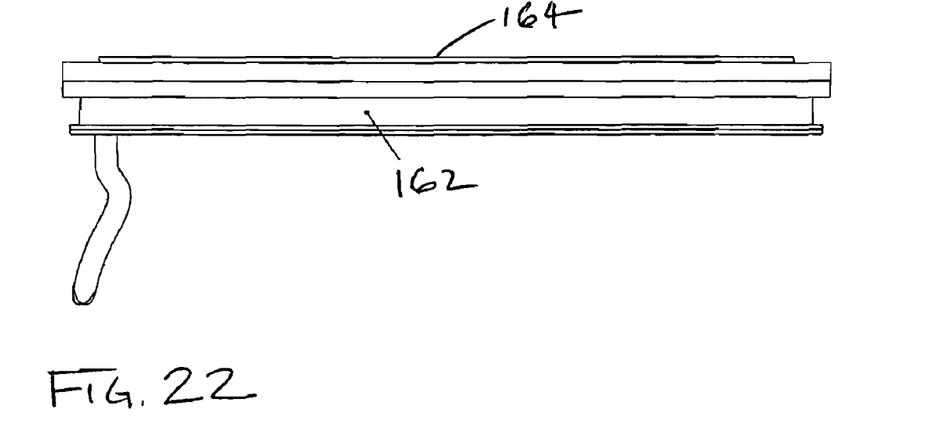
FIG. 22 is a side view of the antenna assembly of FIG. 21.

Referring to FIGS. 15-17, another embodiment of a piling 360 is shown in which suspension assemblies 120A, 120B, shown in detail in FIGS. 18-20 are utilized to hold the sensors 122, 124 for the tip suspension assembly 120A, or the sensors 122, 124 and the radio 160 for the top suspension assembly 120B, in a centered position between the strands 362. As shown in FIGS. 15-17, this allows the use of an antenna assembly 162 that has a smaller profile. The antenna assembly 162, which is shown in FIGS. 21-22 is preferably formed of a polymeric material and includes a removable cover 164 to allow access to the antenna and batteries for powering the radio 160 and the control unit for the sensors 122, 124 on both the tip and top suspension assemblies 120A, 120B. The tip sensors are preferably wired to the control unit located with the top sensors on the top suspension assembly, and data from the sensors at the tip and top can be transmitted using the radio 160 and the antenna assembly 162.

Figure 23:
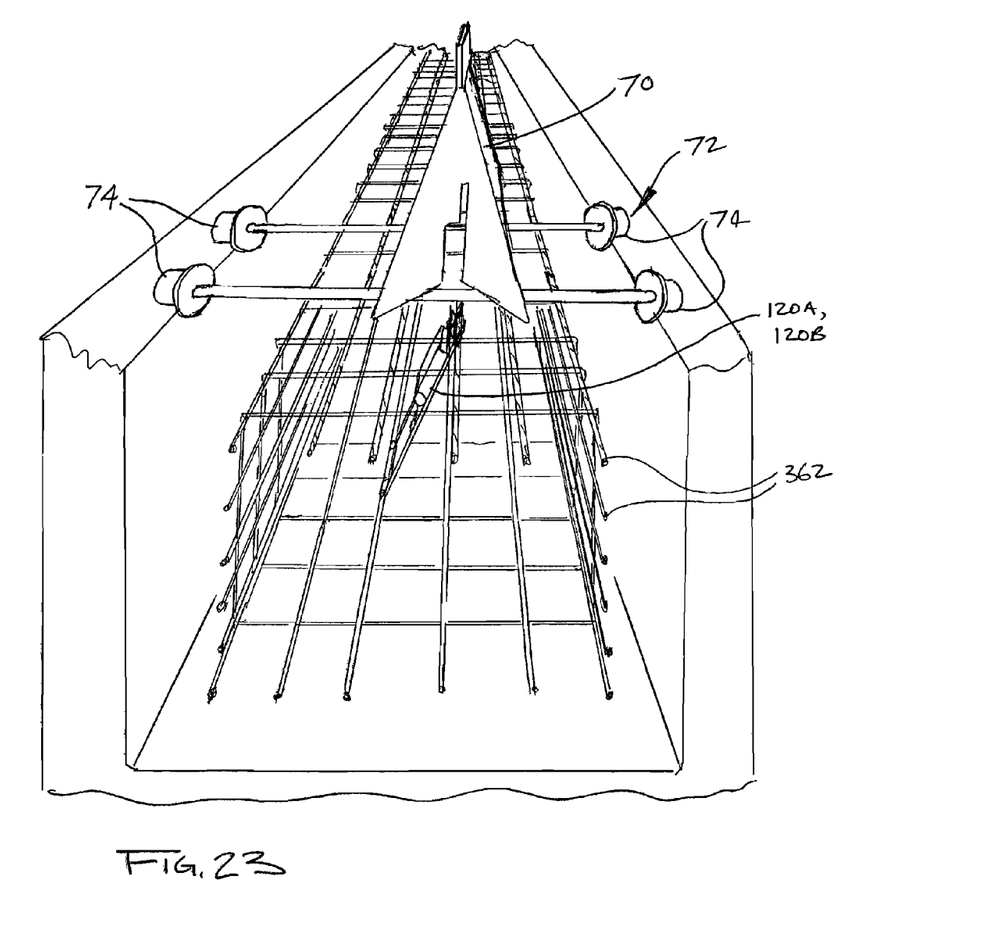
FIG. 23 is a perspective view of a piling form with the strands located therein and a suspension assembly positioned between the strands, and the pour diverter located on a trolley located above the suspension assembly.
Figure 25:
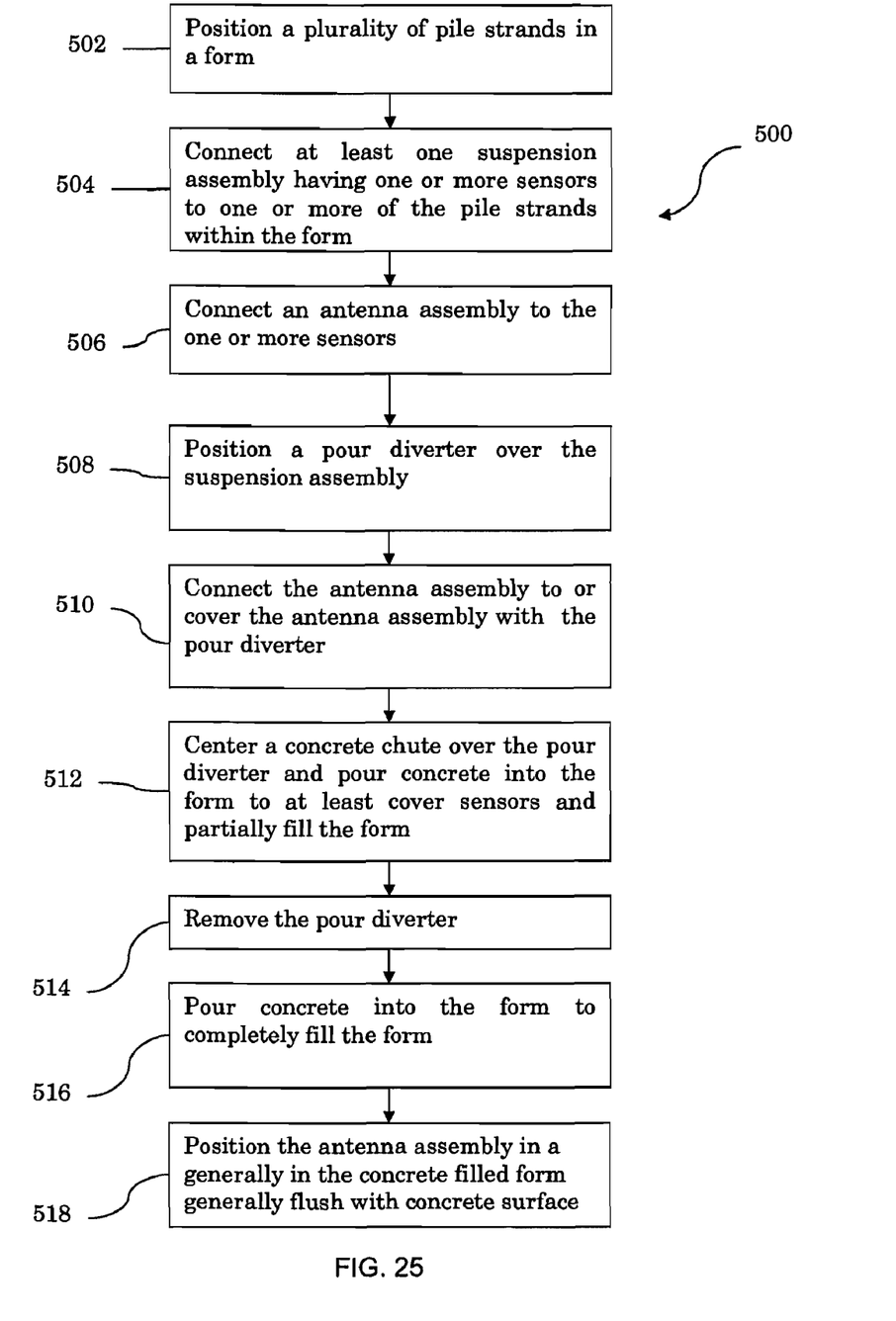
FIG. 25 is a flowchart showing a method for casting a piling according to another preferred embodiment of the present invention.

Referring to FIG. 25, a flow chart describing a method 500 for casting a piling 310 or 360 or a section thereof according to a preferred embodiment of the present invention is shown. The method 500 includes positioning and tensioning a plurality of pile strands 312, 362 in a form (step 502) and connecting a suspension assembly 120 or plurality of suspension assemblies 120A, 120B including one or more sensors 122, 124 to one or more of the pile strands 312 (step 504). An antenna assembly 60 or 162 is connected to the one or more sensors (step 506). In the embodiment of FIGS. 12-14, the antenna assembly includes the radio. For the embodiment of FIGS. 15-17, the antenna assembly 162 is separate from the radio attached to the top suspension assembly 120B. A pour diverter 70 is placed over the suspension assembly 120, 120A, 120B, and can rest on one or more of the strands 312 and associated reinforcement, to protect the sensors during the pour process (step 508), or can be supported or registered on the form, for example as shown in FIG. 23 using a trolley assembly 72 having wheels 74 that allows the diverter to be rolled down the form during the pour to the positions of different suspension assemblies. Sidewall guides can be provided on the form, the trolley 72, or the trolley wheels 74 (for example, in a similar manner to railroad wheels) so that the trolley 72 stays mechanically registered on the form as it is rolled along. Additionally, by using the sidewalls on the top of the form for absolute registration, the antenna assembly 162 can be clipped or held, using a suitable releasable or removable holder, in its flush mount position in the form using the trolley 72 to register its position so that it will be generally flush with a exposed side surface of the piling, so that the concrete can be poured around it to the filled level of the form. The antenna assembly 162 could then be released and the concrete troweled into its finished position so that the antenna assembly 162 is flush with a surface of the piling.

In the embodiment of FIGS. 12-14, the antenna/radio assembly 60 is connected to the pour diverter 70 in a manner in which the antenna/radio assembly 60 preferably assumes a generally vertical position (step 510) in order reduce its exposure during concrete pouring, and the wiring, cables and connectors are also protected by a hollow cover formed by the diverter 70. In the embodiment of FIGS. 15-17, the antenna assembly 162 is preferably located under and covered by the diverter 70 during the pouring of concrete. A concrete chute is centered over the diverter and then concrete is poured into the form (step 512) to at least partially fill the form in and around the sensors/gauges. Preferably, the form is filled to a level just below the diverter 70, or at least covering the sensors/gauges on the suspension assembly 120, 120A, 120B. During the pouring process, concrete can be poured directly over the diverter 70 to fill areas of the form in proximity to the suspension assembly 120. After at least partially filling the form, the pour diverter 70 is removed (step 514).

Then the antenna assembly 60 or 162 is moved to the side, and the form is filled to the desired level with concrete (step 516). The top surface of the antenna assembly is then placed so that it is generally coplanar with the exposed side surface of the piling in the filled form (step 518). This can be done with a tool that forms a cavity that the antenna 150 is then laid into, or can involve placing the antenna 60 with the radio into the concrete as it is being filled to the desired level.

In the preferred embodiment of the invention, the antenna assembly 162 preferably is coated on all sides except the top side with the cover 164 with an epoxy that helps to bond the antenna assembly 162 with the wet concrete. Preferably a disposable foam, rubber, or equivalent ring is located around the rim of the cover 164 and the top of the housing for the antenna assembly 162 that can be removed once the concrete hardens to allow for cover 164 removal. Once the concrete is hardened, the cover 164 is removable for access to the antenna, diagnostic port, test points and batteries located in the antenna assembly 162.

While the preferred embodiments of the invention have been described in detail above, the invention is not limited to the specific embodiments described above, which should be considered as merely exemplary. Further modifications and extensions of the present invention may be developed, and all such modifications are deemed to be within the scope of the present invention as defined by the appended claims.

What is claimed is:

1. A method for casting a piling comprising:
   positioning a plurality of pile strands in a form;
   connecting a suspension assembly having a sensor that is at least one of an accelerometer or a strain gauge to at least one of the pile strands so that the at least one sensor is located in a piling core area;
   positioning a pour diverter over the suspension assembly;
   pouring concrete over the pour diverter, which shields the suspension assembly from a direct flow of the concrete, and into the form; and
   removing the pour diverter.

2. The method of claim 1, wherein the pour diverter splits a flow of the concrete over the suspension assembly so that the concrete fills the form with the concrete on both sides of the suspension assembly until the concrete covers the at least one sensor.

3. The method of claim 1, further comprising completely filling the form with the concrete after removing the pour diverter.

4. The method of claim 1, further comprising, moving the pour diverter along the piling form using a trolley assembly.

5. The method of claim 1, wherein the pour diverter includes:
   two diverter sides arranged in a generally V-shaped configuration;
   a handle portion formed at a position where the two sides join one another; and
   two opposing ends located between the sides, the ends including slots for receiving a portion of a antenna/radio assembly.

6. The method of claim 5, wherein the diverter is formed by two identical formed metal parts that are welded to one another.

7. The method of claim 5, wherein the pour diverter defines a hollow cavity thereunder.

8. The method of claim 5, wherein the handle portion is formed by a slot in a top portion of the two diverter sides.

9. A method for casting a piling comprising:
positioning a plurality of pile strands in a form;
connecting a suspension assembly having a sensor that is at least one of an accelerometer or a strain gauge to at least one of the pile strands so that the at least one sensor is located in a piling core area;
positioning a pour diverter over the suspension assembly;
connecting an antenna assembly to the one or more sensors;
connecting the antenna assembly to or covering the antenna assembly with the pour diverter above a level of the concrete to be poured;
pouring concrete into the form;
removing the pour diverter; and
after the concrete is poured and the diverter is removed, positioning the antenna assembly in the form so that the antenna assembly is generally flush with a surface of the piling.

10. The method of claim 9, further comprising shielding at least one of wires, cables or connectors under the pour diverter.

11. The method of claim 9, further comprising coating an outside of the antenna assembly that is placed in the concrete with an epoxy coating.

* * * * *